United States Patent [19]

Vaughan

[11] 4,218,328
[45] Aug. 19, 1980

[54] LUBRICATING OIL ADDITIVE

[75] Inventor: Ronald J. Vaughan, Orinda, Calif.

[73] Assignee: Chevron Research Company, San Francisco, Calif.

[21] Appl. No.: 973,871

[22] Filed: Dec. 28, 1978

[51] Int. Cl.$^2$ .......................... C10M 1/32; C10M 1/40
[52] U.S. Cl. .................................... 252/33.3; 252/18; 252/25; 252/33.2; 252/34.7; 252/40.5; 252/40.7; 252/42; 252/42.1
[58] Field of Search ................. 252/18, 25, 33.2, 33.3, 252/34.7, 40.5, 40.7, 42, 42.1

[56] References Cited
U.S. PATENT DOCUMENTS

| | | | |
|---|---|---|---|
| 3,524,814 | 8/1970 | Sabol et al. | 252/33.3 X |
| 3,857,790 | 12/1974 | Saunders et al. | 252/40.7 X |
| 4,034,037 | 7/1977 | Jordan | 260/429 R |
| 4,059,536 | 11/1977 | Lallement et al. | 252/33.3 |

Primary Examiner—W. J. Shine
Attorney, Agent, or Firm—D. A. Newell; S. R. LaPaglia; J. J. DeYoung

[57] ABSTRACT

Disclosed is a process for the preparation of a lubricating oil additive which comprises contacting under reaction conditions an amino acid and a basically reacting metal compound. The reaction conditions include the presence of a suspending agent for the basically reacting metal compound and the presence of a hydroxylic promoter. Low-ash, high-alkalinity-value lubricating oil additives are obtainable from the process.

19 Claims, No Drawings

LUBRICATING OIL ADDITIVE

FIELD OF THE INVENTION

This invention relates to a method for preparing lubricating oil additives, particularly overbased lubricating oil additives, to the additives themselves, and to lubricating oil compositions containing the additives.

With the increasing severity of operating conditions of the engines caused in part by the deteriorating quality of fuels for these engines, there is a need for compositions which can lubricate and maintain the cleanliness of the engine while, at the same time, neutralizing large quantities of acids which result from the use of fuels having an increased sulfur content. Conventional lubricating oil additives used to neutralize base contain ash-forming components, generally metallic salts. As increasing amounts of the acid-neutralizing components are used in formulations, the amount of ash in the composition often exceeds the amount of ash for which the engine is designed.

New additives are needed which can maintain the cleanliness of the engine and neutralize the large amounts of acid being formed from the increased use of high-sulfur fuel, while at the same time not exceeding the ash requirements of the engines being lubricated.

The preparation of conventional additives which are overbased to obtain additional acid-neutralizing efficiency is taught in U.S. Pat. No. 3,126,340. The additive described in this patent is prepared by treating a lubricating oil sulfonate dispersant with an alkaline earth metal oxide and hydroxide and then introducing carbon dioxide and ammonia into the mixture followed by heating the mixture in the presence of water to convert the ammonium carbamate formed from the carbon dioxide and ammonia to an alkaline earth metal carbonate. The alkaline earth metal carbonate is the acid-neutralizing portion of the composition.

U.S. Pat. No. 3,524,814 teaches the preparation of an overbased alkaline earth metal sulfonate by introducing a mixture of carbon dioxide and ammonia, in an amount sufficient to form a catalytic amount of ammonium carbamate, into a lubricating oil having in suspension a neutral alkaline earth metal sulfonate containing an alkaline earth oxide. After the catalytic amount of ammonium carbamate is preformed, carbon dioxide is continuously introduced into the reaction mixture until substantially all of the alkaline earth oxide is converted to alkaline earth metal carbonate. The metallic carbonate provides the reserve alkalinity in the sulfonate. As a post-treatment step, water is added to the reaction mixture. The addition of water decomposes any ammonium carbamate still present in the reaction mixture.

U.S. Pat. No. 4,034,037 teaches the production of metal carboxylates or N-organic substituted carbamates by reaction of a carboxylic acid or carbon dioxide with an amine in the presence of a soluble metal salt. These salts are disclosed to be useful as lubricating oil additives.

The production of various alkali and alkaline earth metal salts of N-carboxy amino acids in aqueous and alcohol systems is well known in the art. See, for example, the various articles by M. Siegfried (Z. Physiol. Chem. 44,85 [1905]; 46,401 [1906]; 54,436 [1908] which disclose the production of barium and calcium salts of N-carboxy amino acids. The mercury salts of N-carboxy amino acids are disclosed in C. Neuberg and J. Kerb, Biochemische Z., 40,498 (1912). The sodium salt of N-carboxyglycine is disclosed in A. C. Farthing, J. Chem. Soc. 1950, 3213.

SUMMARY OF THE INVENTION

A process is disclosed for the preparation of a lubricating oil additive which comprises contacting under reaction conditions an amino acid and a basically reacting metal compound, said contacting taking place in the presence of at least one suspending agent for said basically reacting metal compound and in the presence of a hydroxylic promoter.

DETAILED DESCRIPTION OF THE INVENTION

The essential components necessary to produce the additive of the present invention are an amino acid, a basically reacting metal compound, a suspending agent for the basically reacting metal compound, and a reaction-promoting amount of a hydroxylic promoter.

The Amino Acid

The nitrogen portion of the amino acid serves as a source of supply of non-ash-forming basic material in the lubricating oil additives of this invention. By "amino acid" is meant any organic acid containing at least one primary, secondary or tertiary amine (—N<) group and at least one acidic carboxyl (—COOH) group. Mixtures of different amino acids can be used.

Representative amino acids useful in the present invention include: glycine, alanine, beta-alanine, valine, leucine, isoleucine, phenylalanine, serine, threonine, tyrosine, methionine, 6-aminohexanoic acid, proline, hydroxyproline, tryptophan, histidine, lysine, hydroxylysine, arginine, aspartic acid, asparagine, glutamic acid, glutamine, cysteine, cystine, ethylenediaminetetraacetic acid and nitrilotriacetic acid and other alpha-amino acids containing 1 to 5 carboxyl groups.

Particularly preferred are the amino acids which are readily available in commercial quantities such as glycine, beta-alanine, nitrilotriacetic acid, etc. Also particularly preferred are the alpha- or beta-amino acids such as alpha- or beta-alanine.

Numerous processes for the production of amino acids are well known in the art and the amino acids of the present invention can be prepared in situ, if desired. For example, glycine can be prepared from the well-known reaction of ammonia, formaldehyde and potassium cyanide or sodium cyanide. See for example, in U.S. Pat. No. 2,663,713, the disclosure of which is incorporated herein by reference.

The Basically Reacting Metallic Compound

The basically reacting metallic compound is any metallic compound which reacts under basic conditions, i.e., at a pH greater than 7.0, to form a salt of an organic acid. Typical of such metallic compounds are calcium oxide, hydroxide or methoxide, magnesium oxide, hydroxide or methoxide, barium oxide or hydroxide, aluminum hydroxide, sodium hydroxide, lithium hydroxide, sodium alkoxide, and the like. Useful alkoxides are the lower-molecular-weight alkoxides such as methoxide, ethoxide, t-butoxide, and the like. Preferably the oxide or hydroxide of a Group II metal or a Group I metal hydroxide is used.

Preferred lubricating oil additives are prepared from magnesium, barium and calcium oxides or hydroxides, although sodium hydroxide is often desirable in certain applications. Most preferred for use in lubricating oil additives are those compositions prepared from a magnesium or calcium-containing, basically reacting compound, especially calcium oxide, calcium hydroxide, and magnesium oxide.

The Suspending Agent

The suspending agent, which must be oil-soluble, is used to keep the basically reacting metallic component in solution so that it can be an effective portion of the additive composition. Many of the useful suspending agents also have dispersant activity in the final lubricating oil additive composition. Typical suspending agents include alkali metal or alkaline earth metal hydrocarbylsulfonates or fatty acid carboxylates, hydrocarbyl succinimides, hydrocarbyl succinates, hydrocarbyl succinic anhydrides, alkali metal or alkaline earth metal alkylphenates, alkylphenol-type Mannich bases and alkaline earth metal salts of such Mannich bases. Mixtures of suspending agents are also useful in carrying out the process of this invention.

The alkali metal and alkaline earth metal hydrocarbyl sulfonates useful in the process of this invention are well known in the art. The hydrocarbyl group must have a sufficient number of carbon atoms to render the sulfonate molecule oil soluble. Ordinarily, the hydrocarbyl portion has at least 20 carbon atoms and may be aromatic or aliphatic, but is usually alkylaromatic. Certain sulfonates are typically prepared by sulfonating a petroleum fraction having aromatic groups, usually mono- or dialkylbenzene groups, and then forming the metal salt of the sulfonic acid material. Other feedstocks used for preparing these sulfonates include synthetically alkylated benzenes and aliphatic hydrocarbons prepared by polymerizing a mono- or diolefin, for example, a polyisobutenyl group prepared by polymerizing isobutene. The metallic salts are formed directly or by metathesis using well-known procedures.

Succinimide dispersants are also well known in the art, and a general method for their preparation is found in U.S. Pat. Nos. 3,219,666, 3,172,892 and 3,272,746, the disclosures of which are hereby incorporated by reference. These compositions are prepared by reacting an oil-soluble alkyl or alkenyl succinic acid or anhydride with a nitrogen-containing compound. The succinimide may be of the type commonly known as a mono- or bis-succinimide. Preferred nitrogen compounds used in making the succinimides are those known as the ethyleneamines, and particularly preferred are triethylenetetraamine and tetraethylenepentamine. The preferred alkyl or alkenyl groups contain from 50 to 300 carbon atoms, and the most preferred compositions are prepared from polyisobutylene. When this type of suspending agent is employed, the amine portion will contribute to the alkalinity value.

The oil-soluble alkyl or alkenyl succinic anhydrides used in preparing the succinimides are themselves useful as suspending agents; however, they are most preferred for use as co-suspending agents, particularly in combination with a sulfonate suspending agent. Preferably the alkyl or alkenyl portion contains from 50 to 300 carbon atoms.

The succinate esters are prepared by reacting an alcohol with an alkenyl or alkyl succinic anhydride as described above, using a procedure such as that described in U.S. Pat. Nos. 3,381,022 and 3,522,179, the disclosures of which are hereby incorporated by reference. Ordinarily 4 the alkyl or alkenyl group contains from 50 to 300 carbon atoms.

Alkali metal and alkaline earth metal phenates are well known in the art and are the alkali metal or alkaline earth metal salt of an oil-soluble alkyl-substituted phenol. The composition may be sulfurized. Typical phenates are prepared by neutralizing a $C_{8-128}$ alkylphenol with calcium hydroxide or oxide.

Mannich bases are useful suspending agents. Mannich bases are prepared by reacting an oil-soluble phenolic or alcoholic material, such as alkylphenol, with an aldehyde, such as formaldehyde or acetaldehyde, and a nitrogen-containing compound. Typical Mannich bases contain from about 8 to 128 or more carbon atoms in the alkyl group. If desired, the alkaline earth metal salt of the phenolic-type Mannich base may be used as a suspending agent.

Reaction Promoter

A reaction-promoting amount of a hydroxylic promoter is necessary for the reaction to proceed at an acceptable rate. Generally from 0.1 to 10 weight percent or more of the reaction mixture may be the hydroxylic promoter. The promoter is believed to function as a solubilizing agent for the basically reacting metal compound. The promoter is preferably water or an alkanol of 1 to 6 carbon atoms or an alkanediol of 2 to 6 carbon atoms such as methanol, ethanol, isopropanol, butanol, ethylene glycol, 1,4-butanediol and the like. Most preferred are water, ethanol and methanol. Mixtures of these promoters may also be used, chosen so as to keep water formed during the reaction in solution.

Chalcogen Reactant

Although not an essential reactant, it is preferred that the reaction take place in the presence of a chalcogen compound. Suitable chalcogen compounds include carbon dioxide, carbon disulfide, carbon oxysulfide, sulfur dioxide or mixtures thereof. While the chalcogen reactant is ordinarily added in the gaseous form, it may be added in liquid or solid form, for example as dry ice or liquid sulfur dioxide. Carbon dioxide is the preferred chalcogen reactant. When a chalcogen reactant is utilized, the amino acid must contain a primary or secondary amine group. The chalcogen compound is a preferred reactant since it increases the alkalinity value of lubricating oil additives by incorporating more of the basically reacting metallic compound.

Solvent

The reaction is carried out in a suitable solvent. Preferably the solvent is a lubricating oil so that no removal of the solvent is necessary before incorporation of the additive into the lubricating oil. Other useful solvents are lower-boiling hydrocarbon solvents such as hexane or hydrocarbon thinner. Mixtures of lubricating oil with hexane or hydrocarbon thinner are also useful. After preparation is complete, the lower-boiling solvents are readily removed by heating, if desired.

Reaction Conditions

The process of this invention may be carried out at any temperature from the freezing point of the mixture to its boiling point. Ordinarily the reaction is conducted at a temperature of from 0° to 75° C., preferably 20° to 75° C. and most preferably 25° to 50° C. While the reaction proceeds satisfactorily at atmospheric pressure, higher or lower pressures may be used if desired.

The ratio of the basically reacting metallic compound to the chalcogen and the amino acid is such that from about 1/10 to ½ of the alkalinity value of the final composition is contributed by the ashless amino-containing material. Preferably it is desirable to have at least one equivalent of the basically reacting metallic compound for each equivalent of the amino compound. The ratio will vary depending on the structure of the amino acid used and the amount of alkalinity value desired from the ashless nitrogen portion of the amino acid. For a simple amino acid (glycine, beta-alanine), generally at least two equivalents of metallic compound per mol of amino acid are used, whereas for a more complex amino acid (glutamic acid, lysine, nitrilotriacetic acid), generally at least three equivalents are employed, though fewer equivalents may be used if a higher proportion of ashless alkalinity value is desired. Under typical conditions and based on 1 equivalent of the basically reacting metallic compound, the reaction mixture would contain from 0.1 to 2.0, preferably from 0.3–0.5, equivalents of the amino compound; from 0–1, preferably 0.3–0.5, equivalents of chalcogen compound; and from 2 to 20, preferably 4 to 10, parts by weight of the suspending agent per part of the basically reacting metallic compound. The hydrocarbon solvent should be present in sufficient amount to enable good mixing of the reactants and is usually present as from 5 to 50 and preferably 10 to 25 milliliters per gram of basically reacting metallic compound. From 0 to 5, preferably 1 to 2, milliliters of the promoter per gram of basically reacting metallic compound is also used.

In a preferred method for carrying out the reaction, a sodium, calcium or magnesium alkylbenzene sulfonate is used as the suspending agent. It is also preferred to use an alkenylsuccinimide or an alkenylsuccinic anhydride as a co-suspending agent. If this combination of solubilizing agents is used, an increased alkalinity value for the product is obtained when, prior to addition of the amino compound and the basically reacting material, preferably an alkaline earth metal oxide or hydroxide, the mixture of components and the solvent is pretreated with a small amount of chalcogen, for example with from 1 to 10%, preferably about 5%, of the total amount of chalcogen.

Compositions

The compositions prepared by this invention provide a high alkalinity value at a lower ash content than is present in most conventional dispersants and/or acid-neutralizers used as lubricating oil additives.

Alkalinity value is one method of specifying the degree of overbasing of the lubricating oil composition. It is also a measure of the acid-neutralizing properties of the composition. The method for determining the alkalinity value commonly used for a composition is set forth in ASTM Method D-2896. Briefly, the alkalinity value is the total base number given as milligrams of potassium hydroxide per gram of sample. It is the quantity of potassium hydroxide required to neutralize the same amount of perchloric acid that 1 gram of the sample neutralizes. For example, if a composition has the same acid-neutralizing capacity per gram as 10 mg of potassium hydroxide, the composition is given an alkalinity value of 10. The lower limit of alkalinity value is 0 for a neutral composition. Values of 200 or more are especially desirable for use in lubricants which are exposed to the decomposition products of sulfur-containing diesel fuels. Typical alkalinity values for additive compositions of this invention range from about 30 to 400 or more.

Lubricant compositions containing the additives of this invention are prepared by admixing through conventional admixing techniques the appropriate amount of the additive of this invention with a lubricating oil. The selection of a particular base oil depends on the contemplated application of the lubricant and on the presence of other additives. Generally, the amount of additive of this invention used in the lubricating oil will vary from 0.1 to 40% by weight, and preferably from 2 to 35% by weight. The resulting lubricating oil will usually have an alkalinity value in the range of 1 to 120, preferably 2.5 to 100.

The lubricating oil which may be used in this invention includes a wide variety of hydrocarbon oils such as naphthenic bases, paraffin bases and mixed-base oils. The lubricating oils may be used individually or in combination and generally have a viscosity which ranges from 50 to 5000 SUS (Saybolt Universal Seconds) and usually from 100° to 1500° SUS at 38° C.

In many instances it may be advantageous to form concentrates of the additives of this invention within a carrier liquid. These concentrates provide a convenient method of handling and transporting the additives of this invention before their subsequent dilution and use. The concentration of the additives of this invention within the concentrates may vary from 90 to 40% by weight with the oil comprising from 10 to 60% by weight. It is preferred to maintain the concentration of the additives between about 50 and 70% by weight. The preferred method of obtaining concentrates is to carry out the preparation of the additive in a limited amount of lubricating oil, as will be held in making the final dilute lubricant composition. Alternatively, the additive may be prepared in a low-boiling hydrocarbon which is removed by distillation after adding a limited amount of lubricating oil.

As desired, other additives may be included in the lubricating oil compositions of this invention. These additives include antioxidants or oxidation inhibitors, dispersants, rust inhibitors, anticorrosive agents, and so forth. Other types of lubricating oil additives which may be employed include antifoam agents, stabilizers, antistain agents, tackiness agents, antichatter agents, dropping point improvers, antisquawk agents, extreme-pressure agents, odor control agents, and the like.

EXAMPLES

The following examples are presented to illustrate this invention, and are not in any way to be interpreted as limiting the scope of the invention.

EXAMPLE 1

To a 1-liter, 3-neck flask were charged 180 grams of a 67% concentrate of a calcium alkylated aromatic sulfonate in hydrocarbon thinner, 400 ml of a hydrocarbon thinner, 10.3 grams (0.25 mol) magnesium oxide (Maglite A, Merck, 200 $m^2/g$), 18.8 grams (0.25 mol) glycine and 10.0 ml water. The mixture was stirred at room temperature and warmed to 40° C. and then 3 grams of carbon dioxide was added over a 25-minute period at a temperature of from 40° to 45° C. Then 10 ml of 100% ethanol was added and 2 grams of carbon dioxide was added over a period of 20 minutes at temperatures ranging from 45° to 55° C. An additional 5 ml of 100% ethanol was added and an additional 8 grams of carbon dioxide was added over a period of 76 minutes at 55° C. The reaction mixture was then centrifuged for 20 minutes at 12,000 RPM and then filtered throgh a pad of diatomaceous earth. The filtrate was stripped to 110° C. at 20 mm Hg pressure. The mixture yielded 142 grams of product having an alkalinity value of 189.8, and containing 3.22% magnesium, 1.33% calcium, and 1.24% nitrogen.

EXAMPLE 2

To a 5-liter, 3-neck flask was charged 670 grams of a 67% concentrate of a calcium alkylated aromatic sulfonate in hydrocarbon thinner, 2330 grams of a hydrocarbon thinner, 47 ml water, 75 ml 95% ethanol, 50.5 grams magnesium oxide, and 94.0 grams glycine. The mixture was stirred and heated to 40° C. 56 grams of carbon dioxide was added over 2 hours, 15 minutes while the temperature ranged from 38° to 47° C. The reaction mixture was filtered through a pad of diatomaceous earth. The filtrate was stripped to 110° C. at 20 mm Hg pressure. The mixture yielded 826 grams of product having an alkalinity value of 203.6 and containing 3.08% magnesium, 1.38% calcium, and 1.39% nitrogen.

EXAMPLE 3

To a 1-liter, 3-neck flask was charged 150 grams of a 67% concentrate of a calcium alkylated aromatic sulfonate in hydrocarbon, 450 ml of a hydrocarbon thinner, 20 ml of methanol, 10 ml of water, 37.5 grams glycine (0.5 mol) and 20.6 grams magnesium oxide. The mixture was stirred and heated to 45° C. and 25 grams of carbon dioxide was added over 5 hours and 13 minutes while the temperature ranged from 33° C. to 48° C. The reaction mixture was filtered through a pad of diatomaceous earth. The filtrate was stripped to 110° C. at 20 mm Hg pressure. The mixture yielded 184 grams of product having an alkalinity value of 282.4 and containing 4.94% magnesium, 1.27% calcium, and 1.8% nitrogen.

EXAMPLE 4

To a 500-ml Erlenmeyer flask was charged 4.03 grams (0.10 mol) magnesium oxide (Velsicol), 60.0 grams of a 67% concentrate of a calcium alkylated aromatic sulfonate in hydrocarbon thinner, 200 ml of a hydrocarbon thinner, 5 ml water and 10 ml of methanol. The mixture was then stirred and 12.73 grams nitrilotriacetic acid was added. The mixture was then stirred vigorously at room temperature overight. A small portion was then centrifuged for 30 minutes at 11,000 RPM. The resultant clear supernatant had an alkalinity value of 10.84.

EXAMPLE 5

To a 500-ml Erlenmeyer flask was charged 4.03 grams magnesium oxide (0.1 mol) (Velsicol), 60.0 grams of a 67% concentrate of a calcium alkylated aromatic sulfonate in hydrocarbon thinner and 200 ml of a hydrocarbon thinner. The mixture was then stirred and 14.6 grams (0.05 mol) ethylenediaminetetraacetic acid was added. The mixture was then stirred at room temperature overnight and the reaction mixture was filtered through a pad of diatomaceous earth. The resultant clear filtrat. had an alkalinity value of 10.07.

EXAMPLE 6

To a 5-liter, 3-neck flask was charged 900 grams of a 67% concentrate of a calcium alkylated aromatic sulfonate in hydrocarbon thinner, 2300 ml of a hydrocarbon thinner, 120 ml of methanol, 120 ml of water, 210 grams (2.8 mols) glycine and 153.2 grams (3.8 mols) magnesium oxide. The mixture was stirred for 5 minutes at room temperature and then 126 grams of carbon dioxide and 30 ml of water were added over 8 hours with the temperature ranging from 28° to 41° C. The reaction mixture was filtered through a pad of diatomaceous earth. The filtrate was stripped to 115° C. at 20 mm Hg pressure. The mixture yielded 1188 grams of product having an alkalinity value of 332.6, and containing 5.98% magnesium, 1.04% calcium and 2.05% nitrogen.

EXAMPLE 7

To a 1-liter, 3-neck flask was charged 160 grams of a 67% concentrate of a calcium alkylated aromatic sulfonate hydrocarbon thinner, 400 ml of a hydrocarbon thinner, 15 ml methanol, 8.0 grams (0.2 mol) magnesium oxide, and 7.9 grams ammonium bicarbonate. Then over a 10-minute period 9.8 grams (0.2 mol) of sodium cyanide and 16.2 grams of a 37% formaldehyde solution were slowly added. The mixture was warmed to 40° C. and stirred for 3¼ hours. Then 2 ml of 37% formaldehyde was added and 1 ml of water and the mixture stirred for another 95 minutes. Then 11 grams of carbon dioxide was added over a period of 66 minutes at temperatures ranging from 50° to 55° C. The reaction mixture was stripped to 130° C. (bottoms), 95° C. (overhead). The product was filtered through a pad of diatomaceous earth. The filtrate was stripped to 110° C. at 20 mm Hg pressure. The reaction mixture yielded 182 grams of product having an alkalinity value of 120.0 and containing 1.41% magnesium, 1.12% calcium, 1.27% nitrogen and 1.60% sodium.

What is claimed is:

1. A process for the preparation of a lubricating oil additive which comprises contacting under reaction conditions a mixture of an amino acid and a basically reacting metal compound, said contacting taking place in the presence of a solvent and at least one suspending agent for said basically reacting metal compound and in the presence of a hydroxylic promoter, said reaction conditions including a temperature from the freezing point to the boiling point of the mixture and based on one equivalent of the basically reacting metallic compound from 0.1 to 2.0 equivalents of the amino acid and from 2 to 20 parts by weight of the suspending agent per part of the basically reacting metal compound.

2. The process of claim 1 wherein said amino acid is an alpha-amino acid.

3. The process of claim 2 wherein said alpha-amino acid contains 1 to 5 carboxyl groups.

4. The process of claim 3 wherein said amino acid is glycine.

5. The process of claim 1 wherein said basically reacting metal compound is a Group I metal hydroxide or Group II metal oxide or hydroxide.

6. The process of claim 1 wherein said suspending agent is an alkali metal or alkaline earth metal hydrocarbylsulfonate, a hydrocarbylsuccinimide, a hyrocarbylsuccinate, a hydrocarbylsuccinic anhydride, an alkali metal or alkaline earth metal alkylphenate, a Mannich base or an alkaline earth metal salt of a Mannich base, or mixtures thereof.

7. The process of claim 6 wherein said suspending agent is an alkali metal or alkaline earth metal hydrocarbylsulfonate, a hydrocarbylsuccinimide or a hydrocarbylsuccinic anhydride, or mixtures thereof.

8. The process of claims 1, 2, 3, 4, 5, 6 or 7 wherein said amino group contains a primary or secondary amine group and said contacting takes place in the presence of carbon dioxide, carbon disulfide, carbon oxysulfide or sulfur dioxide.

9. The process of claim 8 wherein said contacting takes place in the presence of carbon dioxide.

10. The process of claim 1 wherein said hydroxylic promoter is water, methanol, ethanol or mixtures thereof.

11. The process of claim 1 wherein said amino acid is prepared in situ.

12. The process of claim 11 wherein said amino acid is glycine and is prepared in situ from the reaction of ammonia, formaldehyde, and sodium or potassium cyanide.

13. A process of the preparation of a lubricating oil additive which comprises contacting under reaction conditions a mixture of an amino acid selected from glycine, alpha-or beta-alanine, cystine, methionine or lysine and a basically reacting metal compound selected from calcium oxide or hydroxide, magnesium oxide or hydroxide, lithium or sodium hydroxide, said contacting taking place in the presence of a solvent and at least one suspending agent for said basically reacting compound, at least one chalcogen compound selected from carbon dioxide, carbon disulfide, carbon oxysulfide or sulfur dioxide, and in the presence of a promoting amount of a hydroxylic promoter, said reaction conditions including a temperature from the freezing point to the boiling point of the mixture and based on one equivalent of the basically reacting metallic compound from 0.1 to 2.0 equivalents of the amino acid and from 2 to 20 parts by weight of the suspending agent per part of the basically reacting metal compound.

14. The process of claim 13 wherein said amino acid is glycine, said basically reacting metal compound is calcium hydroxide or magnesium oxide, and said chalcogen is carbon dioxide.

15. The product prepared by the process of claims 1, 2, 3, 4, 5, 6, 7, 13 or 14.

16. A lubricating oil composition comprising an oil of lubricating viscosity and from 0.1 to 40% by weight of a product according to claim 15.

17. A lubricating oil concentrate which comprises from 10 to 60% by weight of an oil of lubricating viscosity and from 90 to 40% by weight of a product according to claim 16.

18. The product prepared by the process of claim 8.

19. The product prepared by the process of claim 9.

* * * * *